US009339579B2

(12) United States Patent
Willette (10) Patent No.: US 9,339,579 B2
(45) Date of Patent: May 17, 2016

(54) MINI-ULTRAVIOLET LIGHT SYSTEM

(71) Applicant: Triatomic Environmental, Inc., Jupiter, FL (US)

(72) Inventor: Christopher C. Willette, Tequesta, FL (US)

(73) Assignee: Triatomic Environmental, Inc., Jupiter, FL (US)

( * ) Notice: Subject to any disclaimer, the term of this patent is extended or adjusted under 35 U.S.C. 154(b) by 356 days.

(21) Appl. No.: 13/745,189

(22) Filed: Jan. 18, 2013

(65) Prior Publication Data

US 2013/0192288 A1  Aug. 1, 2013

Related U.S. Application Data (60) Provisional application No. 61/588,415, filed on Jan. 19, 2012.

(51) Int. Cl.
*A61L 9/20* (2006.01)

(52) U.S. Cl.
CPC ............. *A61L 9/20* (2013.01); *A61L 2209/111* (2013.01); *A61L 2209/16* (2013.01)

(58) Field of Classification Search
CPC ................ A61L 2209/111; A61L 2209/16; A61L 9/20
USPC .......................................... 62/264; 422/186.3
See application file for complete search history.

(56) References Cited

U.S. PATENT DOCUMENTS

| 4,956,754 | A  | * | 9/1990 | Chen ............................ 362/101 |
| 5,525,520 | A  | * | 6/1996 | Dinh ............................ 436/126 |
| 6,679,068 | B1 | * | 1/2004 | Guzorek .......................... 62/78 |
| 2002/0008214 | A1 | * | 1/2002 | sevack et al. ............. 250/504 R |
| 2003/0000229 | A1 | * | 1/2003 | Underwood ...................... 62/78 |
| 2006/0066191 | A1 | * | 3/2006 | Bschorer et al. .............. 313/110 |
| 2007/0059225 | A1 | * | 3/2007 | Willette ..................... 422/186.3 |
| 2008/0048541 | A1 | * | 2/2008 | Sumrall et al. ................ 313/112 |
| 2010/0092346 | A1 | * | 4/2010 | Jeon .............................. 422/122 |
| 2014/0084185 | A1 | * | 3/2014 | Palmer et al. ............. 250/504 R |

FOREIGN PATENT DOCUMENTS

DE  10209994 A1 * 9/2003 ............ F24F 3/1405

* cited by examiner

*Primary Examiner* — Emmanuel Duke
(74) *Attorney, Agent, or Firm* — McHale & Slavin P.A.

(57) ABSTRACT

A contamination control system for ductless air conditioners is disclosed. The contamination control system may be formed from one or more decontamination lamps contained within a tubular housing that is hollow and includes an internal cavity extending from the first end to the second end with at least one longitudinally extending sight window positioned between first and second tubular end regions. The decontamination lamp may be positioned within the internal cavity in the tubular housing. The tubular housing may be held in place with a mounting system including at least one tubular housing receiver in which the tubular housing is secured. The tubular housing is slidably held within the mounting system such that the tubular housing is slidable longitudinally relative to the tubular housing receivers and is rotatable within the tubular housing receivers. The decontamination lamp may be activated with a photo activated sensor.

20 Claims, 7 Drawing Sheets

TEST RESULTS

| LOCATION | BEFORE CFU/UNIT | AFTER CFU/UNIT | % REDUCTION |
|---|---|---|---|
| LEFT SIDE BLOWER | 110,000 | 9,300 | 91.5 |
| LEFT SIDE BACK WALL | 1,600,000 | 450 | 99.9 |
| RIGHT SIDE BLOWER | 23,000 | <10 | 99.9 |
| RIGHT SIDE BACK WALL | 20,000 | <10 | 99.9 |

MINI-ULTRAVIOLET LIGHT SYSTEM

CROSS-REFERENCE TO RELATED APPLICATION

This patent application claims priority to U.S. Provisional Patent Application No. 61/588,415, filed Jan. 19, 2012, which is incorporated by reference in its entirety.

FIELD OF THE INVENTION

This disclosure is directed generally to contamination control systems, and more particularly, to contamination control systems for air conditioners.

BACKGROUND

Ductless air condition systems, which are often referred to as mini-splits, are formed from an air conditioning system without ducts, thereby enabling the systems to be placed into tight spaces in which conventional window or ducted systems do not fit. The ductless air conditioning systems are often formed from an outdoor condenser and an indoor air handler. The condenser supplies coolant to the air handler through refrigerant lines that run from outside a structure to the indoor air handler inside the structure. The air handler pulls air into the unit through a front grill, passes the air through evaporator coils and exhausts the newly-cooled air back into the room in the structure. The environment within the internal air handler is susceptible to the growth of mold and bacteria and the collection of airborne biological contaminants such as germs, viruses, pollen and allergens. Thus, the environment within the internal air handler needs to be controlled to limit such growth.

SUMMARY

A contamination control system for ductless air conditioners is disclosed. The contamination control system may be formed from one or more decontamination lamps contained within a tubular housing that is hollow and includes an internal cavity extending from a first end to a second end with a longitudinally extending sight window positioned between the first and second ends. The decontamination lamp may be positioned within the internal cavity in the tubular housing. The tubular housing may be held in place with a mounting system including at least one tubular housing receiver in which the tubular housing is secured. The tubular housing is slidably held within the mounting system such that the tubular housing is slidable longitudinally relative to the tubular housing receiver and is rotatable within the tubular housing receiver. The decontamination lamp may be activated with a photo activated sensor.

The contamination control system may include one or more tubular housings having a first end and a second end positioned generally opposite to the first end, wherein the tubular housing is hollow and includes an internal cavity extending from the first end to the second end and wherein the tubular housing includes at least one longitudinally extending sight window positioned between first and second tubular end regions.

The contamination control system may include one or more decontamination lamps positioned within the internal cavity in the tubular housing. In at least one application, the contamination control system may include three or more lamps. The decontamination lamp may be a shielded ultraviolet lamp capable of emitting germicidal ultraviolet light and less than ½" diameter. In at least one embodiment, the decontamination lamp may be about ⅜" in diameter. The decontamination lamp may also be formed from first and second decontamination lamps.

The contamination control system may include a mounting system including at least one tubular housing receiver in which the tubular housing is secured, wherein the at least one tubular housing receiver creates opposing first and second pressure points that engage the tubular housing. In at least one embodiment, the tubular housing receiver of the mounting system may include a first receiver having a planar mounting surface and first and second arms extending orthogonally away from a backside of the planar mounting surface. The first arm may include the first pressure point and the second arm includes the second pressure point. A second receiver may have a planar mounting surface and first and second arms extending orthogonally away from a backside of the planar mounting surface. The first arm may include the first pressure point and the second arm includes the second pressure point. The first receiver may be in contact with the first tubular end region of the tubular housing and the second receiver may be in contact with the second tubular end of the tubular housing, wherein the tubular housing is slidably held within the mounting system such that the tubular housing is slidable longitudinally relative to the first and second receivers and is rotatable within the first and second receivers.

The contamination control system may include a shock absorption collar positioned between the tubular housing and the decontamination lamp contained within the tubular housing to protect the decontamination lamp. The contamination control system may also include a component protection system that encloses the first end of the tubular housing and seals electrical components coupled to the decontamination lamp to prevent exposure to moisture.

The contamination control system may include a photo activated sensor configured to connect the decontamination lamp to a power source when the sensor perceives the presence of light. The contamination control system may also include a power supply including at least one rectifier. The power supply may operate at 120 volts, 208 volts, 240 volts and the like.

An advantage of the contamination control system is that the contamination control system inhibits mold growth on the HVAC interior surfaces. In particular, the contamination control system is specifically configured to prevent the collection of contamination from occurring on the blower wheel, exhaust or supply vents and prevents contamination from being exhausted from the ductless systems.

Another advantage of the contamination control system is that the multiple tubular housings forming the tubular housing system for the decontamination lamps enables the system to be installed in wide range of air conditioners having different sizes.

Yet another advantage of the contamination control system is that the contamination system saves energy and reduces maintenance costs through reduction or elimination of contamination.

Another advantage of the contamination control system is that the contamination system reduces airborne microbial contaminants.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

As shown in FIGS. 1-22, a contamination control system 10 for ductless air conditioners 12 is disclosed. The contamination control system 10 may be formed from one or more decontamination lamps 16, as shown in FIGS. 1, 3, 8-10, 12 and 16, contained within a tubular housing 22 that is hollow and includes an internal cavity 24 extending from a first end 26 to a second end 28 with a longitudinally extending sight window 30 positioned between the first and second ends 26, 28. The decontamination lamp 16 may be positioned within the internal cavity 24 in the tubular housing 22. The tubular housing 22 may be held in place with a mounting system 32 including at least one tubular housing receiver 34 in which the tubular housing 22 is secured. The tubular housing 22 is slidably held within the mounting system 32 such that the tubular housing 22 is slidable longitudinally relative to the tubular housing receiver 34 and is rotatable within the tubular housing receiver 34. The decontamination lamp 16 may be activated with a photo activated sensor 36.

The contamination control system 10 may be configured to be mounted within ductless air conditioners 12, as shown in FIGS. 2 and 5-11. Typically, ductless air conditioners 12 are mounted indoors and are shielded from weather. The ductless air conditioner 12 may have any appropriate configuration and may include an air conditioning compressor 38 coupled to a heat exchanger 40 and contained within a housing 42 supporting a fan 44. The fan 44 may be, but is not limited to being, a centrifugal fan 44 positioned in close proximity to an exhaust opening 46. The opening 46 may include one or more louvers directing the flow of cooled air from the ductless air conditioner 12.

As shown in FIGS. 1, 3, 8-10, 12 and 16, the contamination control system 10 may be formed from a tubular housing 22 having a first end 26 and a second end 28 positioned generally opposite to the first end 22. The tubular housing 22 may be hollow and may include an internal cavity 24 extending from the first end 26 to the second end 28. The tubular housing 22 may include at least one longitudinally extending sight window 30 positioned between first and second tubular end regions 48, 50. The longitudinally extending sight window 30 may be configured such that side edges 52, 54 of the longitudinally extending sight window 30 are positioned approximately up to 180 degrees apart from each other when viewed axially. In other embodiments, the longitudinally extending sight window 30 may be narrower such that the side edges 52, 54 are spaced closer together.

Figure 16:
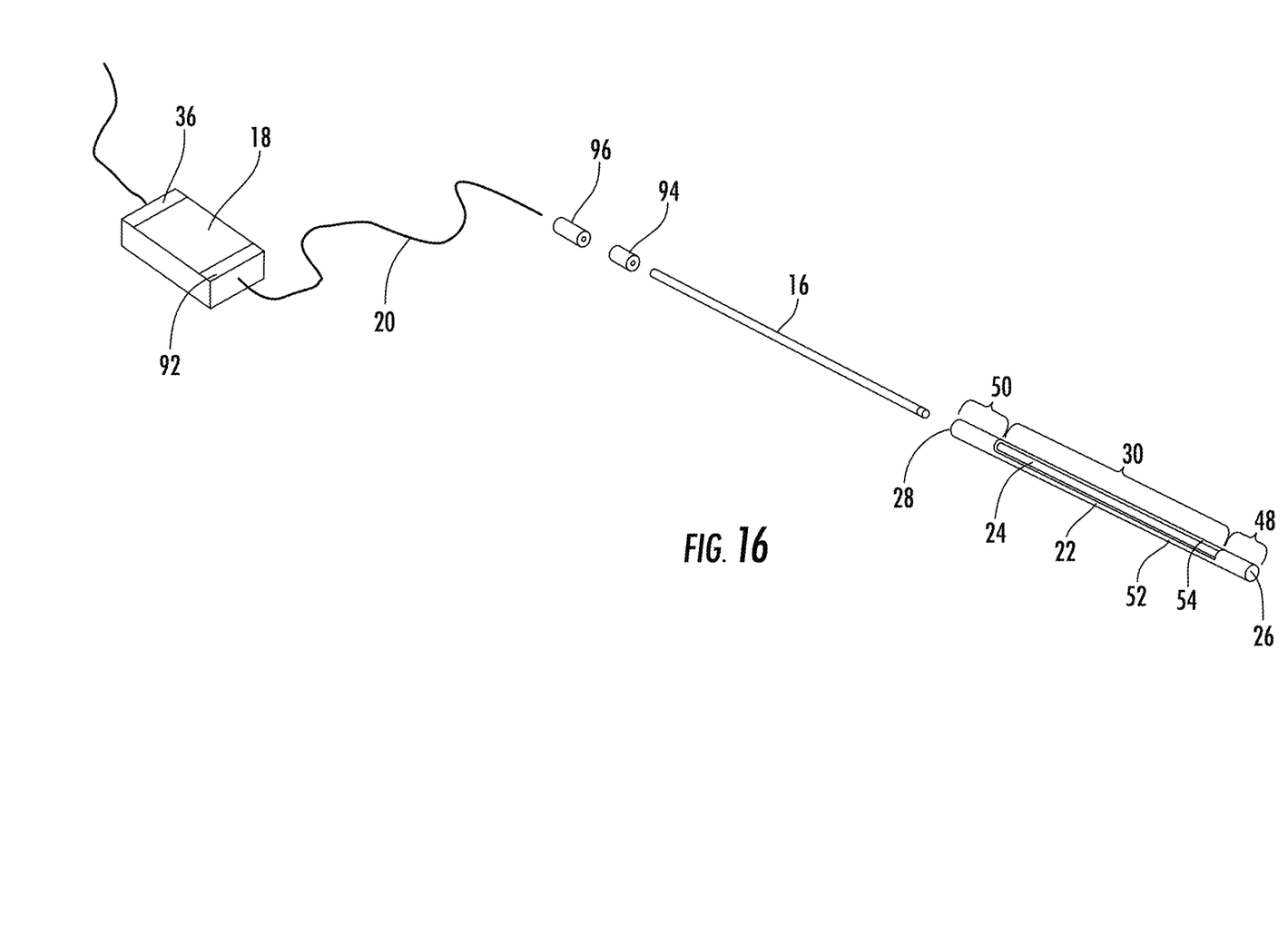
FIG. 16 is an exploded view of the contamination control system.
Figure 17:
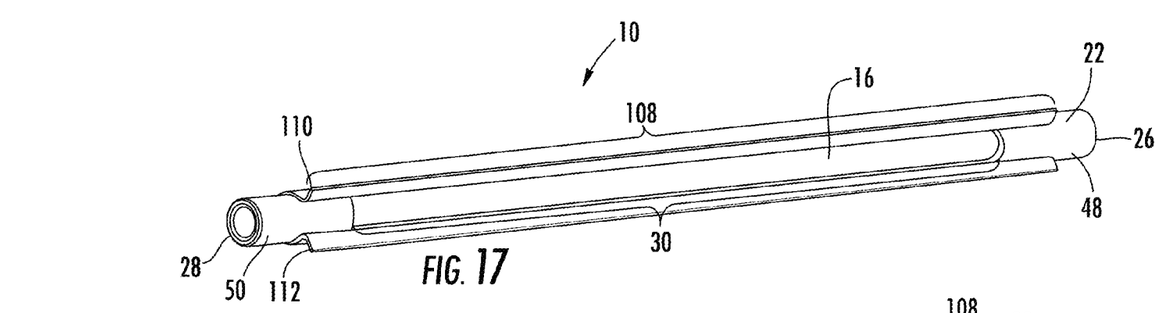
FIG. 17 is a perspective view of another embodiment of the tubular housing of the contamination control system.
Figure 18:
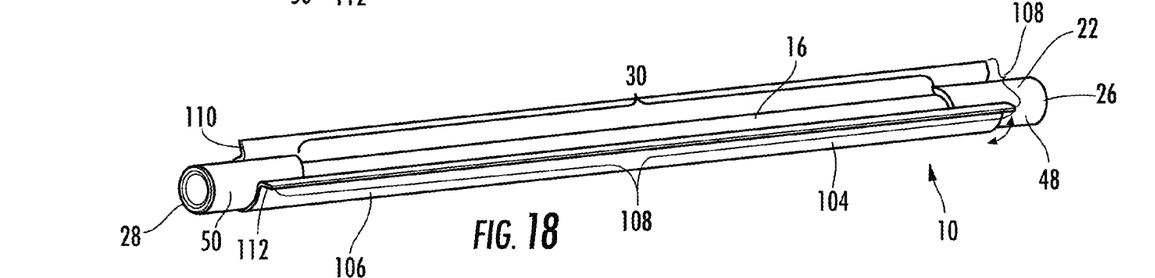
FIG. 18 is a perspective view of the embodiment of the tubular housing of the contamination control system shown in FIG. 17 with the decontamination lamp shield rotated.
Figure 19:
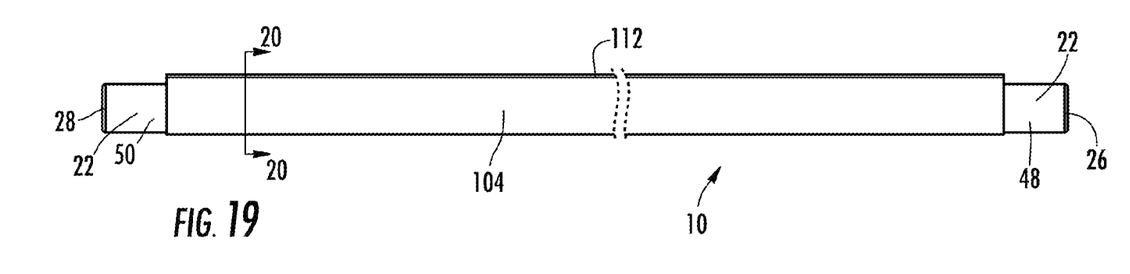
FIG. 19 is a side view of the embodiment of the tubular housing of the contamination control system shown in FIG. 17.

One or more decontamination lamps 16, as shown in FIG. 16, may be positioned within the internal cavity 24 in the tubular housing 22. The decontamination lamp 16 may be a shielded ultraviolet lamp capable of emitting germicidal ultraviolet light and may be less than ½" diameter. In at least one embodiment, the decontamination lamp 16 may be about ⅜" in diameter. In one embodiment, the decontamination lamp 16 may be between about five inches and about 15 inches in length and may be between about ¼" and about ½" in diameter. The decontamination lamps 16 may be sized to fit within the indoor air handler 14. In at least one embodiment, the contamination control system 10 may include two or more tubular housings 22 each including one or more decontamination lamps 16, as shown in FIGS. 1, 3, 8-10, 12 and 16. In one embodiment, the contamination control system 10 may include a first tubular housing 56 with one or more the decontamination lamps 16 and a second tubular housing 58 with one or more decontamination lamps 16. Use of the first and second tubular housings 56, 58 enables the contamination control system 10 to be positioned in any appropriate position within the housing 42 of the ductless air conditioner 12 such that the ultraviolet light emitted from the decontamination lamps 16 passes through air emitted from the fan 44. In such a configuration, the contamination control system 10 may include first and second decontamination lamps 60, 62. The contamination control system 10 may include two or more lamps 16.

Figure 1:
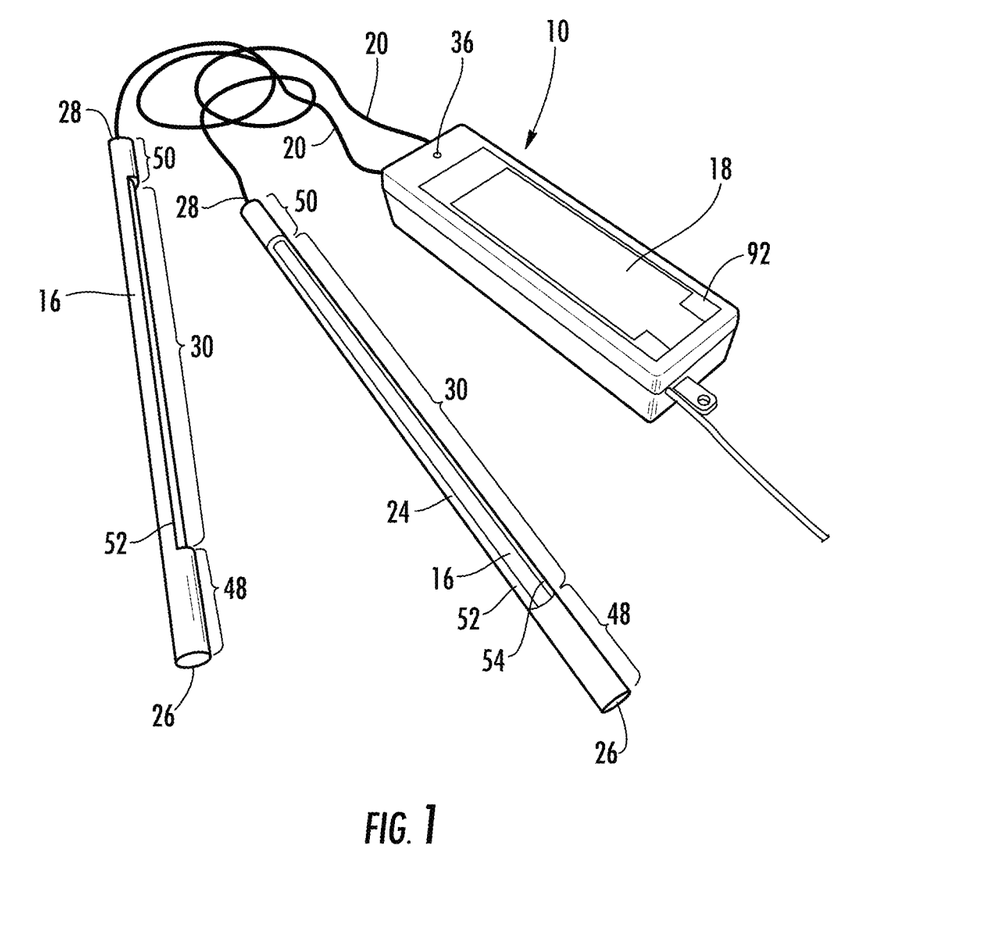
FIG. 1 is a perspective view of the contamination control system.
Figure 2:
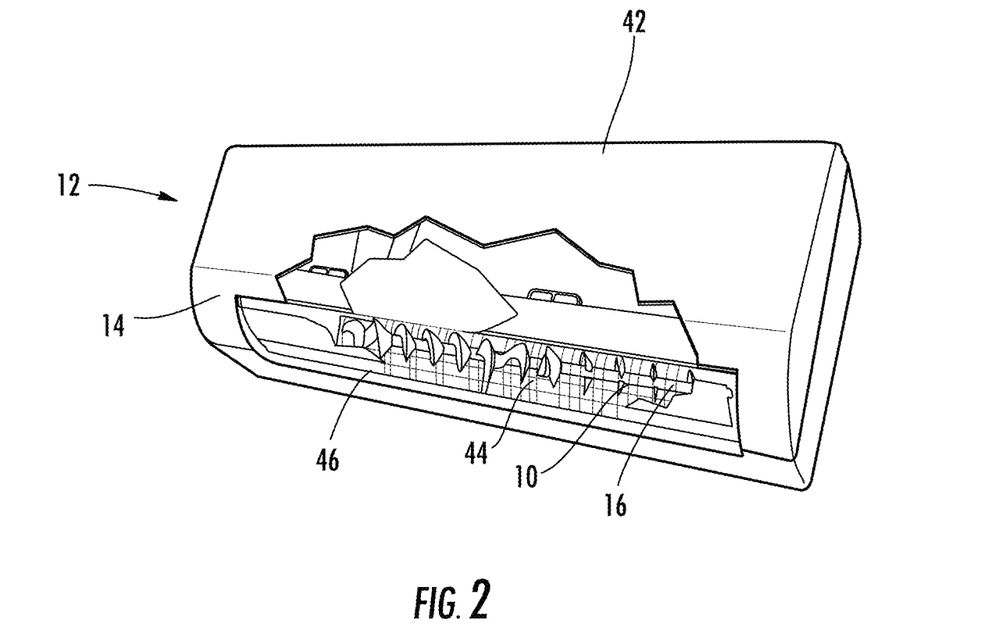
FIG. 2 is a partial perspective view of a ductless air condition system containing the contamination control system.
Figures 3, 4, 5, 6, 7, 8, 9, 10:
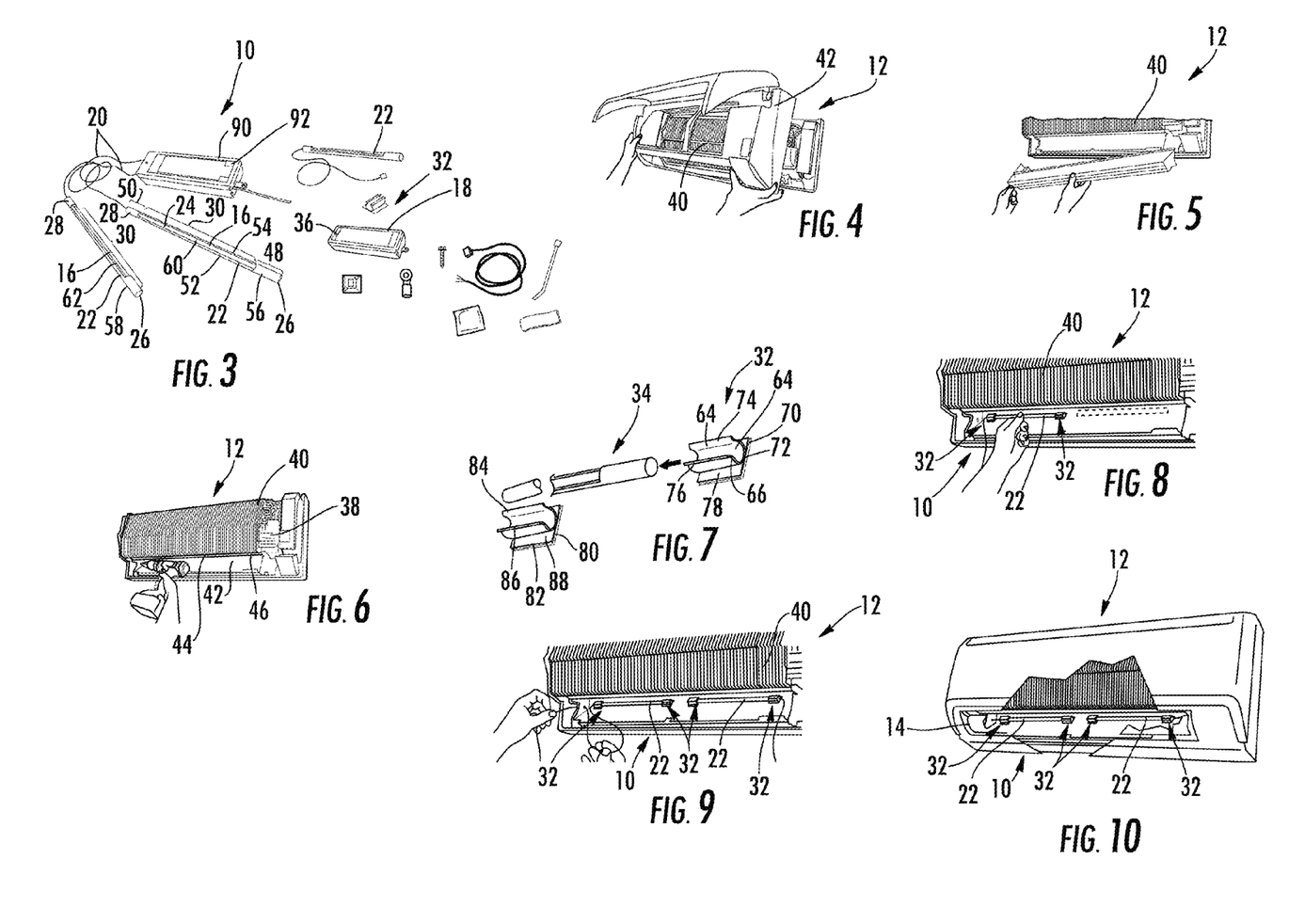
FIG. 3 is an exploded view of the components forming the contamination control system.
FIG. 4 is a perspective view of a ductless air conditioner having the housing removed to install the contamination control system.
FIG. 5 is a partial perspective view of the ductless air conditioner having the housing removed to install the contamination control system.
FIG. 6 is a perspective view of a ductless air conditioner having the housing removed to install the contamination control system.
FIG. 7 is a partial, exploded view of tubular housing and a mounting system.
FIG. 8 is a perspective view of a ductless air conditioner with the housing removed and a contamination control system being installed therein.
FIG. 9 is a perspective view of a ductless air conditioner with the housing removed and a contamination control system formed from two tubular housings.
FIG. 10 is a perspective view of a ductless air conditioner with the housing installed and a contamination control system formed from two tubular housings.
Figure 11:
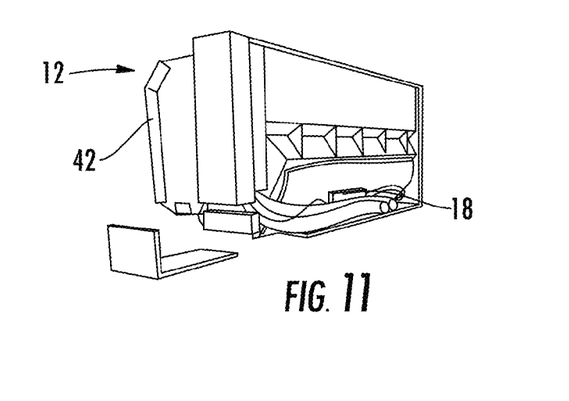
FIG. 11 is a perspective, rear view of a ductless air conditioner with a contamination control system.
Figure 12:
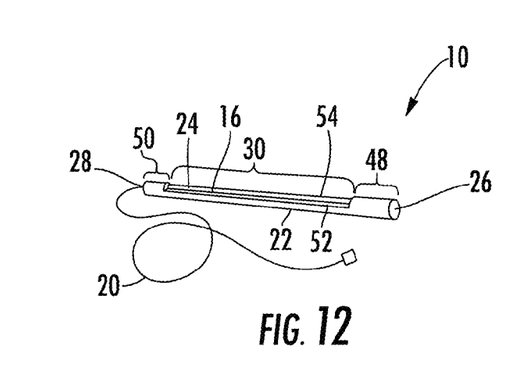
FIG. 12 is a perspective view of a tubular housing of a contamination control system.

As shown in FIGS. 7-10 and 22, the contamination control system 10 may also include a mounting system 32 including at least one tubular housing receiver 64 in which the tubular housing 22 is secured. As shown in FIG. 7, the tubular housing receiver 64 may create opposing first and second pressure points 66, 68 that engage the tubular housing 22. The tubular housing receiver 64 of the mounting system 32 may include a first receiver 70 having a planar mounting surface 72 and first and second arms 74, 76 extending orthogonally away from a backside 78 of the planar mounting surface 72. The first arm 74 may include the first pressure point 66, and the second arm 76 may include the second pressure point 68. A second receiver 80 may include a planar mounting surface 82 and first and second arms 84, 86 extending orthogonally away from a backside 88 of the planar mounting surface 72. The first arm 84 may include the first pressure point 66, and the second arm 86 may include the second pressure point 68. The first receiver 70 may be in contact with the first tubular end region 48 of the tubular housing 22, and the second receiver 80 may be in contact with the second tubular end region 50 of the tubular housing 22. The tubular housing 22 may be slidably held within the mounting system 32 such that the tubular housing 22 is slidable longitudinally relative to the first and second receivers 70, 80 and is rotatable within the first and second receivers 70, 80. As such, the direction of the ultraviolet light emitted from the decontamination lamp 16 through the longitudinally extending sight window 30 may be changed as desired and adjusted for use in any ductless air conditioner 12, whether a new application or a retrofit on an existing ductless air conditioner 12.

Figure 20:
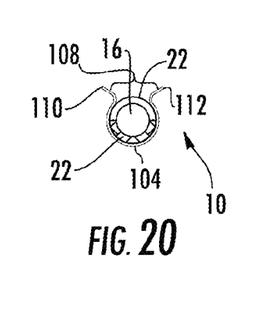
FIG. 20 is a cross-sectional view of the tubular housing taken at section line 20-20 in FIG. 19.

As shown in FIGS. 17-20, the contamination control system 10 may also include a decontamination lamp shield 104 that is adjustable to change an amount of exposure of the decontamination lamp 16. The decontamination lamp shield 104 may be formed from a partially cylindrical housing 106 having an elongated slot 108 formed by first and second opposing flanges 110, 112. The cylindrical housing 106 resides radially outward from the tubular housing 22 and is rotatable relative to the tubular housing 22, thereby enabling the longitudinally extending sight window 30 to be adjusted. The elongated slot 108 formed by the first and second flanges 110, 112 of the decontamination lamp shield 104 may have a width defined by the first and second flanges 110, 112 being separated by less than 180 degrees, as shown in FIG. 20. As such, the first and second flanges 110, 112 prevent the decontamination lamp shield 104 from being accidently removed from the tubular housing 22. In at least one embodiment, the first and second flanges 110, 112 may be separated about 179 degrees and the first and second flanges 110, 112 may flex to enable the decontamination lamp shield 104 to be installed on or removed from the tubular housing 22. In another embodiment, the first and second flanges 110, 112 may be separated by 150 degrees or less and require that the decontamination lamp shield 104 be slide onto the tubular housing 22 from an end. Such configuration may prevent the decontamination lamp shield 104 from being removed from the tubular housing 22. An internal diameter of the decontamination lamp shield 104 may be slightly larger than an outer diameter of the tubular housing 22. In at least one embodiment, the internal diameter of the decontamination lamp shield 104 may be approximately equal to the outer diameter of the tubular housing 22, thereby creating resistance to rotating the decontamination lamp shield 104 while in place. The decontamination lamp shield 104 may be formed from a material, such as, but not limited to, aluminum, galvanized steel, stainless steel, plastic and the like.

Figure 13:
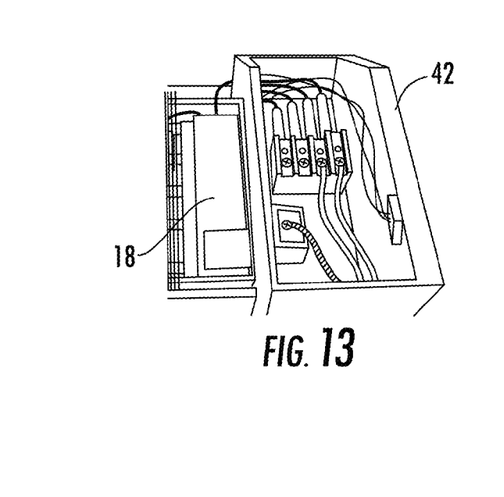
FIG. 13 is a perspective view of a power supply mounted to a ductless air conditioner.
Figure 14:
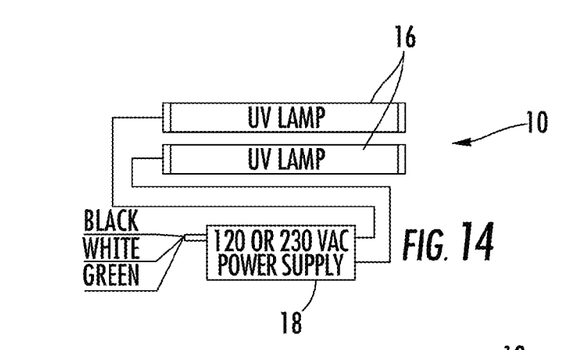
FIG. 14 is a schematic view of decontamination lamps coupled to a power supply.
Figure 15:
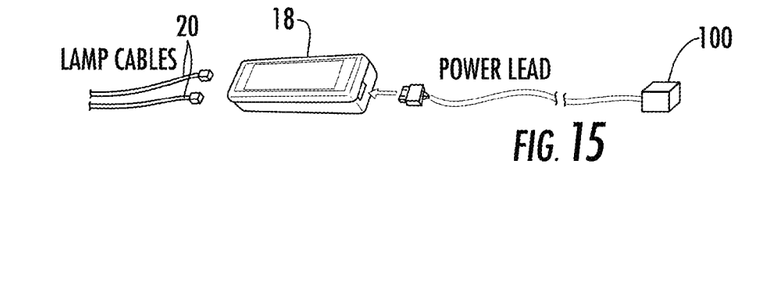
FIG. 15 is an exploded view of a power supply coupled to a power source.

The contamination control system 10 may also include a power supply 18 configured to provide power to the system 10, as shown in FIGS. 1, 3 and 14-16. The power supply 18 may be any appropriate power supply. In at least one embodiment, the contamination control system 10 is configured to operate on direct current (DC) and is configured to be attachable to a conventional publically available power system. In such an embodiment, the power supply 18 may include one or more rectifiers 92 configured to convert the alternating current (AC) to DC power usable by the contamination control system 10. In at least one embodiment, the power supply may operate at 120 volts. Operation of the decontamination lamps 16 may be controlled by a photo activated sensor 36 configured to connect the decontamination lamp 16 to a power source 100 when the sensor 36 perceives the presence of light, thereby turning the decontamination lamp 16 on. The power source 100, as shown in FIG. 15, may be any source of power. The power supply 18 may be configured with a photo activated sensor 36 to only operate the power supply 18 when the room is lighted, such as with daylight or room lights and shut off the power supply 18 when the room is dark. The power supply 18 may include attachment mechanisms to provide flexible mounting options. The power supply 18 may be in electrical communication with the decontamination lamps 16 via one or more wires 20, which may be insulated. The power supply 18 may be coupled to a power source 100 via a number of configurations, one of which is shown in FIG. 13.

The contamination control system 10 may also include a shock absorption collar 94, as shown in FIG. 16, positioned between the tubular housing 22 and the decontamination lamp 16 contained within the tubular housing 22 to protect the decontamination lamp 16. In at least one embodiment, the shock absorption collar 94 may be formed from materials, such as, but not limited to, silicone. The shock absorption collar 94 may be formed before being inserted into position in the tubular housing 22, and, in another embodiment, may be formed in place in the tubular housing 22. The contamination control system 10 may also include a component protection system 96 that encloses the first end 26 of the tubular housing 22 and seals electrical components coupled to the decontamination lamp 16 to prevent exposure to moisture. The component protection system 96 may be formed from materials, such as, but not limited to, silicone, and other waterproofing materials.

Figure 21:
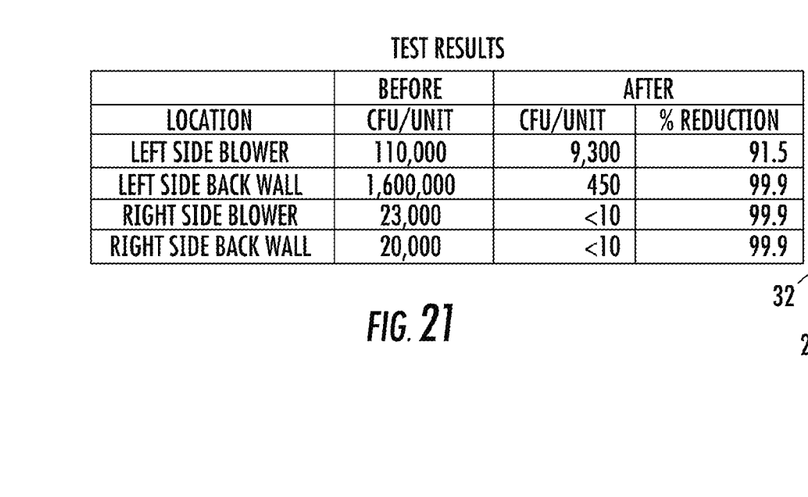
FIG. 21 is a graph displaying the results of using the contamination control system in a ductless air conditioner to kill colony forming units (CFU).
Figure 22:
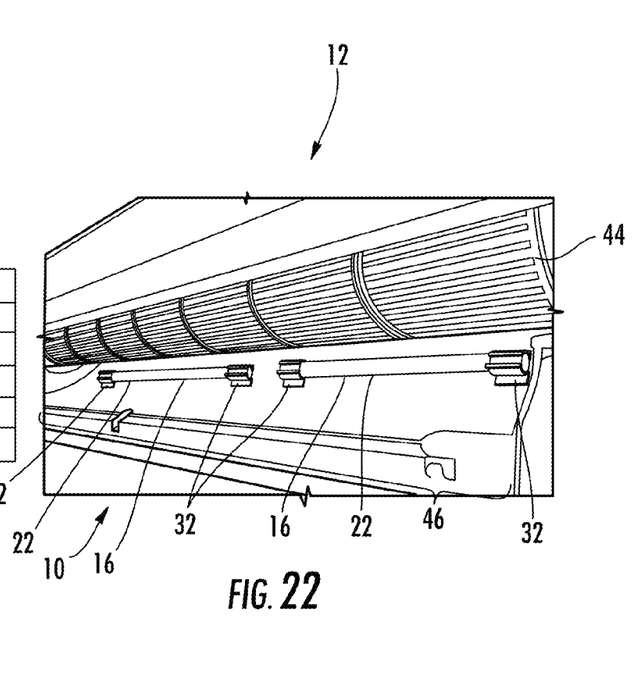
FIG. 22 is a perspective view of a ductless air conditioner with the housing installed and a contamination control system formed from two tubular housings.

The contamination control system 10 may be used to decontaminate cooled air exhausted from an air conditioning system 12, such as, but not limited to, a ductless air conditioning system. In at least one embodiment of the contamination control system 10, first and second tubular housings 56, 58 may be positioned immediately downstream of the fan 44 and positioned such that the longitudinally extending sight window 30 faces the fan 44, thereby exposing the fan blades of the fan 44 and the air exhausted from the fan 44 to the ultraviolet light. Such exposure to the ultraviolet light kills bacteria and other microbes within the air, as shown in FIG. 21 displaying the effectiveness on colony forming units (CFUs). Use of the first and second tubular housings 56, 58 enables the contamination control system 10 to be used with any sized air conditioning system 12. In particular, in an air conditioning system 12 with a small width less than a combined distance of lengths of the first and second tubular housings 56, 58, the first and second tubular housings 56, 58 may be positioned parallel to each other, orthogonal to the flow of air exhausted from the fan and positioned immediately downstream of the fan 44. In other embodiments in which the air conditioning system 12 has a width greater than a combined distance of lengths of the first and second tubular housings 56, 58, the first and second tubular housings 56, 58 may be aligned with each other and placed end to end, may be positioned to be orthogonal to the flow of air exhausted from the fan and positioned immediately downstream of the fan 44. The contamination control system 10 may be operated manually or automatically.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A contamination control system for air conditioners, comprising:
   a tubular housing having a first end and a second end positioned generally opposite to the first end, wherein the tubular housing is hollow and includes an internal cavity extending from the first end to the second end and wherein the tubular housing includes at least one longitudinally extending sight window positioned between first and second tubular end regions;
   a decontamination lamp positioned within the internal cavity in the tubular housing, at least a portion of said decontamination lamp positioned within said internal cavity is exposed to said sight window, whereby light emitted from said decontamination lamp passes through said sight window;
   a mounting system including at least one tubular housing receiver in which the tubular housing is secured, wherein the tubular housing is slidably held within the mounting system such that the tubular housing is slidable longitudinally relative to a first and second receivers and is rotatable within the first and second receivers, wherein the at least one tubular housing receiver creates opposing first and second pressure points that engage the tubular housing;
   a shock absorption collar positioned between the tubular housing and the decontamination lamp contained within the tubular housing to protect the decontamination lamp;
   a decontamination lamp shield having a partially cylindrical housing rotatably coupled to said tubular housing, whereby rotation of said decontamination lamp shield relative to said sight window adjusts an amount of exposure of light emitted from the decontamination lamp through said sight window; and
   a photo activated sensor configured to connect the decontamination lamp to a power source when the sensor perceives the presence of light.

2. The contamination control system of claim 1, wherein said partially cylindrical housing having an elongated slot formed by first and second opposing flanges, wherein the cylindrical housing resides radially outward from the tubular housing.

3. The contamination control system of claim 2, wherein the elongated slot formed by the first and second flanges of the decontamination lamp shield has a width defined by the first and second flanges being separated by less than 180 degrees.

4. The contamination control system of claim 1, further comprising a component protection system that encloses the first end of the tubular housing and seals electrical components coupled to the decontamination lamp to prevent exposure to moisture.

5. The contamination control system of claim 1, further comprising a power supply operating at 120 volts.

6. The contamination control system of claim 1, wherein the tubular housing receiver of the mounting system comprises a first receiver having a planar mounting surface and first and second arms extending orthogonally away from a backside of the planar mounting surface, wherein the first arm include the first pressure point and the second arm includes the second pressure point, and a second receiver having a planar mounting surface and first and second arms extending orthogonally away from a backside of the planar mounting surface, wherein the first arm include the first pressure point and the second arm includes the second pressure point.

7. The contamination control system of claim 6, wherein the first receiver is in contact with the first tubular end region of the tubular housing and the second receiver is in contact with the second tubular end of the tubular housing, wherein the tubular housing is slidably held within the mounting system such that the tubular housing is slidable longitudinally relative to the first and second receivers and is rotatable within the first and second receivers.

8. The contamination control system of claim 1, wherein the decontamination lamp is a shielded ultraviolet lamp capable of emitting germicidal ultraviolet light and less than ½" diameter.

9. The contamination control system of claim 8, wherein the decontamination lamp has a ⅜" diameter.

10. The contamination control system of claim 1, wherein the decontamination lamp comprises first and second decontamination lamps.

11. A ductless air conditioning system, comprising:
    an air conditioning compressor coupled to a heat exchanger and contained within a housing supporting a fan;
    a contamination control system comprising:
    a tubular housing having a first end and a second end positioned generally opposite to the first end, wherein the tubular housing is hollow and includes an internal cavity extending from the first end to the second end and wherein the tubular housing includes at least one longitudinally extending sight window positioned between first and second tubular end regions;
    a decontamination lamp positioned within the internal cavity in the tubular housing, at least a portion of said decontamination lamp positioned within said internal cavity is exposed to said sight window;
    a mounting system including at least one tubular housing receiver in which the tubular housing is secured, wherein the tubular housing is slidably held within the mounting system such that the tubular housing is slidable longitudinally relative to a first and second receivers and is rotatable within the first and second receivers, wherein the at least one tubular housing receiver creates opposing first and second pressure points that engage the tubular housing;
    a shock absorption collar positioned between the tubular housing and the decontamination lamp contained within the tubular housing to protect the decontamination lamp;
    a decontamination lamp shield that is adjustable to change an amount of exposure of the decontamination lamp, wherein the decontamination lamp shield is a partially cylindrical housing having an elongated slot formed by first and second opposing flanges, wherein the cylindrical housing resides radially outward from the tubular housing and is rotatable relative to the tubular housing, thereby enabling the longitudinally extending sight window to be adjusted; and
    a photo activated sensor configured to connect the decontamination lamp to a power source when the sensor perceives the presence of light.

12. The contamination control system of claim 11, wherein the elongated slot formed by the first and second flanges of the decontamination lamp shield has a width defined by the first and second flanges being separated by less than 180 degrees.

13. The ductless air conditioning system of claim 11, further comprising a component protection system that encloses the first end of the tubular housing and seals electrical components coupled to the decontamination lamp to prevent exposure to moisture.

14. The ductless air conditioning system of claim 11, further comprising a power supply operating at 120 volts.

15. The ductless air conditioning system of claim 11, wherein the tubular housing receiver of the mounting system comprises a first receiver having a planar mounting surface and first and second arms extending orthogonally away from a backside of the planar mounting surface, wherein the first arm include the first pressure point and the second arm includes the second pressure point, and a second receiver having a planar mounting surface and first and second arms extending orthogonally away from a backside of the planar mounting surface, wherein the first arm include the first pressure point and the second arm includes the second pressure point.

16. The ductless air conditioning system of claim 15, wherein the first receiver is in contact with the first tubular end region of the tubular housing and the second receiver is in contact with the second tubular end of the tubular housing, wherein the tubular housing is slidably held within the mounting system such that the tubular housing is slidable longitudinally relative to the first and second receivers and is rotatable within the first and second receivers.

17. The ductless air conditioning system of claim 11, wherein the decontamination lamp is a shielded ultraviolet lamp capable of emitting germicidal ultraviolet light and less than ½" diameter.

18. The ductless air conditioning system of claim 11, wherein the decontamination lamp comprises first and second decontamination lamps.

19. A contamination control system for air conditioners, comprising:
  a tubular housing having a first end and a second end positioned generally opposite to the first end, wherein the tubular housing is hollow and includes an internal cavity extending from the first end to the second end and wherein the tubular housing includes at least one longitudinally extending sight window positioned between first and second tubular end regions;
  a decontamination lamp positioned within the internal cavity in the tubular housing, at least a portion of said decontamination lamp positioned within said internal cavity is exposed to said sight window;
  a mounting system including at least one tubular housing receiver in which the tubular housing is secured, wherein the at least one tubular housing receiver creates opposing first and second pressure points that engage the tubular housing;
  a decontamination lamp shield having a partially cylindrical housing rotatably coupled to said tubular housing, whereby rotation of said decontamination lamp shield relative to said sight window adjusts an amount of exposure of light emitted from the decontamination lamp through said sight window, whereby light emitted from said decontamination lamp passes through said sight window;
  a shock absorption collar positioned between the tubular housing and the decontamination lamp contained within the tubular housing to protect the decontamination lamp;
  a photo activated sensor configured to connect the decontamination lamp to a power source when the sensor perceives the presence of light;
  a component protection system that encloses the first end of the tubular housing and seals electrical components coupled to the decontamination lamp to prevent exposure to moisture;
  a power supply that operates at 120 volts;
  wherein the tubular housing receiver of the mounting system comprises a first receiver having a planar mounting surface and first and second arms extending orthogonally away from a backside of the planar mounting surface;
  wherein the first arm includes the first pressure point and the second arm includes the second pressure point, and a second receiver having a planar mounting surface and first and second arms extending orthogonally away from a backside of the planar mounting surface;
  wherein the first arm include includes the first pressure point and the second arm includes the second pressure point;
  wherein the first receiver is in contact with the first tubular end region of the tubular housing and the second receiver is in contact with the second tubular end of the tubular housing; and
  wherein the tubular housing is slidably held within the mounting system such that the tubular housing is slidable longitudinally relative to the first and second receivers and is rotatable within the first and second receivers.

20. The contamination control system of claim 19, wherein the decontamination lamp is a shielded ultraviolet lamp capable of emitting germicidal ultraviolet light and less than ½" diameter and wherein the decontamination lamp comprises first and second decontamination lamps.

* * * * *